(12) United States Patent
Guillaume

(10) Patent No.: US 6,216,885 B1
(45) Date of Patent: *Apr. 17, 2001

(54) TRAY FOR GROUPING TOGETHER ARTICLES

(75) Inventor: Christophe Guillaume, Saint-Ismier (FR)

(73) Assignee: Becton Dickinson France, S.A., Le Pont de Claix (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/015,843

(22) Filed: Jan. 29, 1998

(30) Foreign Application Priority Data

Nov. 27, 1997 (FR) .................................... 97 15184

(51) Int. Cl.⁷ ................................ B65D 83/10; A47F 7/00
(52) U.S. Cl. ..................... 211/85.13; 211/60.1; 206/366; 206/564
(58) Field of Search ............... 211/85.13, 60.1; 206/366, 364, 365, 564

(56) References Cited

U.S. PATENT DOCUMENTS

| | | | |
|---|---|---|---|
| 1,496,873 | * | 6/1924 | Dean .................................... 211/60.1 |
| 2,084,540 | * | 6/1937 | Smith .................................... 206/365 |
| 2,856,067 | * | 10/1958 | Sparks .................................... 206/366 |
| 2,887,215 | * | 5/1959 | Hutchison .................................... 206/365 |
| 3,133,635 | * | 5/1964 | Gordon et al. .................................... 206/366 |
| 3,305,084 | * | 2/1967 | Higgins et al. .................................... 206/366 |
| 3,589,511 | * | 6/1971 | Brit .................................... 206/564 X |
| 3,606,006 | * | 9/1971 | Raybois .................................... 206/564 |
| 3,707,227 | * | 12/1972 | Britt .................................... 206/43 X |
| 4,005,776 | * | 2/1977 | Seeley .................................... 206/364 X |
| 4,015,709 | * | 4/1977 | Millet .................................... 206/366 |
| 4,085,845 | * | 4/1978 | Perfect .................................... 206/564 |
| 4,333,567 | * | 6/1982 | Leonard .................................... 206/366 X |
| 4,383,615 | * | 5/1983 | Aquino .................................... 211/60 R |
| 4,572,371 | * | 2/1986 | Asenbauer .................................... 206/564 X |
| 4,593,816 | * | 6/1986 | Langenbeck .................................... 206/564 X |
| 5,048,684 | * | 9/1991 | Scott .................................... 206/364 |
| 5,139,746 | * | 8/1992 | Rabenecker .................................... 422/104 |
| 5,156,267 | * | 10/1992 | Yates, Jr. et al. .................................... 206/364 |
| 5,199,567 | * | 4/1993 | Discko, Jr. .................................... 206/369 |
| 5,350,564 | * | 9/1994 | Mazza et al. .................................... 422/63 |
| 5,360,109 | * | 11/1994 | Janota .................................... 206/564 X |
| 5,558,222 | * | 9/1996 | Volk et al. .................................... 206/564 X |
| 5,681,539 | * | 10/1997 | Riley .................................... 422/300 |
| 5,993,745 | * | 11/1999 | Laska .................................... 422/104 |

FOREIGN PATENT DOCUMENTS 24 35 672 A1    2/1976   (DE) .
0 790 063 A1    8/1997   (EP) .

* cited by examiner

Primary Examiner—Daniel P. Stodola
Assistant Examiner—Khoa Tran
(74) Attorney, Agent, or Firm—Allen W. Wark

(57) ABSTRACT

Trays for grouping together articles, for example syringes which are to be filled, and the tray including a flattened body, with the body being elongate in a first direction, and a plurality of housings which are open on the first face for the articles, respectively, each arranged in a second, transverse direction, the housings being distributed in the first direction. The flattened body includes a plurality of gripping studs, designed to come into contact with, respectively, gripping suction cups, arranged and distributed over the second face, the studs each including flats whose level is located inside the flattened body.

7 Claims, 5 Drawing Sheets

TRAY FOR GROUPING TOGETHER ARTICLES

FIELD OF THE INVENTION

The present invention generally relates to trays, and more specifically relates to a tray for grouping together elongated articles, particularly cylindrical articles, such as for example syringes which are to be filled with medicinal products such as drugs, medicines, medicaments and the like.

BACKGROUND OF THE INVENTION

Trays for transporting and manipulating syringes to be filled with medicinal products, for example medicinal products in liquid form, are already known, and are being produced from a variety of materials for example from a sheet of thermo-formed plastic including an elongated body, of rectangular shape, which has a first face, for example an upper face, and a second face, for example a lower face, which are opposite each other, the body of which extends in a first direction, or length, and in a second, transverse direction, or width; and a plurality of housings which are open on the first face to receive and hold the cylindrical articles, for example the cylindrical bodies of the syringes which are to be filled; these housings are each arranged in the second, transverse direction, or width, being distributed in the first direction, or length; each housing includes opposite protuberances which move back in one direction for the insertion of the corresponding article and which, in the other direction, hold the same article, for example against gravity.

However, several limitations and disadvantages are associated with such trays, including the fact that it is not possible to manipulate such trays, containing the syringes which are to be filled satisfactorily, particularly with means or devices for gripping or manipulating. As the tray has limited intrinsic rigidity, it is difficult to manipulate it with mechanical means. Use is therefore made of means of pneumatic type, using suction. To this end, the trays, loaded with syringes, may be manipulated by means of their second face, or lower face, i.e., in an upside-down position, with a gripping head which establishes a vacuum or suction in the enclosure limited by the border of the elongated body. According to this technique, it appears to be difficult to establish a good seal between the suction head and the border of the elongated body of the tray, which is likely, in particular, to become deformed without guaranteeing said seal.

According to another technique, vacuum pads are applied at various points on the tray, with the tray loaded with the grouped-together articles being in an upside-down position. However, these vacuum pads do not allow reliable gripping, for various reasons, including they are applied to an irregular surface, for example a warped surface, with respect to which it is difficult to create a good seal; the aging of the rubber made vacuum pads makes it impossible to guarantee a uniform carrying force over time; and the deformability of the tray may break the seal with each vacuum pads. In fact, any kind of poor gripping or manipulation of the grouping tray which is loaded with articles may cause the tray and possibly the articles to be damaged, or alternatively cause the tray and the articles to be dropped. Such accidents can cause the production line which is fed with the articles grouped together on the trays to be shut down or otherwise stopped.

Thus, there has been a need for a tray which would eliminate the problems and limitations associated with the prior trays discussed above.

SUMMARY OF THE INVENTION

In contrast to the prior trays discussed above, it has been found that the tray of the present invention allows secure manipulation or gripping with vacuum pads despite the tray's lack of rigidity, particularly when it is produced from a thermo-formed plastic material, irrespective of the load borne by the tray in the form of the articles grouped together on it.

In accordance with the present invention, the elongated body of the grouping tray includes a plurality of gripping studs, designed to later come into contact with, respectively, vacuum pads of handling equipment, arranged and distributed over the second face of the elongated body. In addition, said studs each comprise one flat area whose level is located inside the flattened body, that is to say above the support plane of the tray, determined by the edge or border of said body when its first face is the upper face, and under the top plane of the tray.

In the preferred embodiment of the tray for grouping together elongate articles, for example syringes which are to be filled, the tray includes an elongated body which includes a first face and a second face which are opposite each other, the body being elongate in a first direction and a plurality of housings which are open on the first face for the articles, respectively each arranged in a second, transverse direction, the housings being distributed in the first direction, each housing including opposite protuberances which move back or otherwise deflect in one direction for the insertion of the corresponding article and which, in the other direction, hold the same article, wherein the elongated body includes a plurality of gripping studs designed to come into contact with, respectively, gripping vacuum pads, arranged and distributed over the second face with the studs each including flat area whose level is located inside the elongated body.

BRIEF DESCRIPTION OF THE DRAWINGS

The various features, objects, benefits, and advantages of the present invention will become more apparent upon reading the following detailed description of the preferred embodiment(s) along with the appended claims in conjunction with the drawings, wherein like reference numerals identify corresponding components, and:

DETAILED DESCRIPTION OF THE PREFERRED EMBODIMENT

Figure 1:
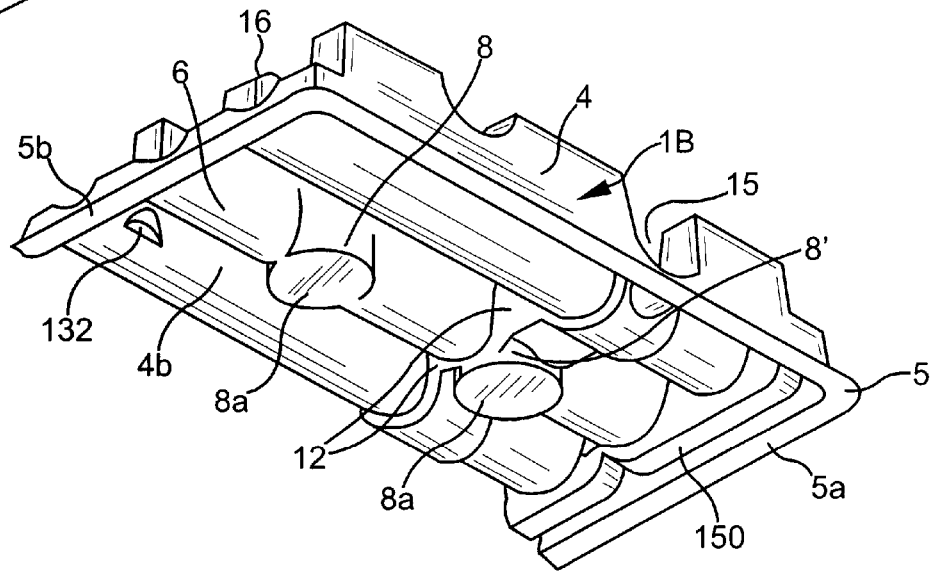
FIG. 1 is a perspective, fragmentary view of a pair of trays according to the present invention prior to being stacked one on top of the other in an alternating position.
Figure 1:
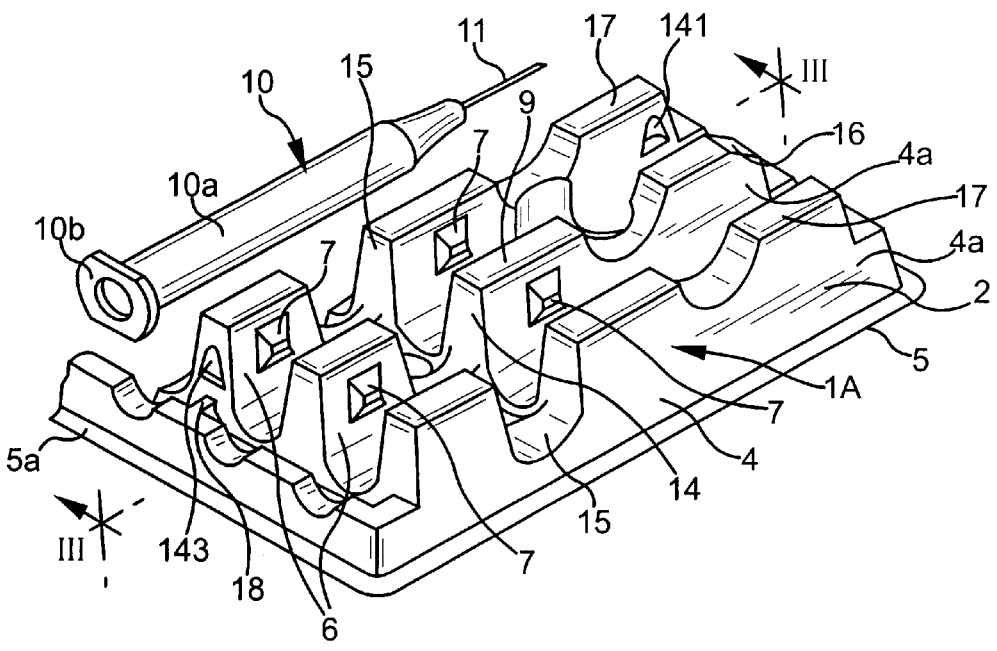

The tray of the present invention is illustrated in FIGS. 1–6 and generally includes the designation 1. Referring to FIGS. 1–5, the tray 1 of the present invention is intended for grouping together elongated articles, which in the preferred embodiment includes syringes 10 which are to be filled. As illustrated in FIG. 1, each of the syringes 10 includes a body 10a which is provided with a proximal collar 10b and a distal needle 11 inserted in the proximal end thereof.

Figure 2:
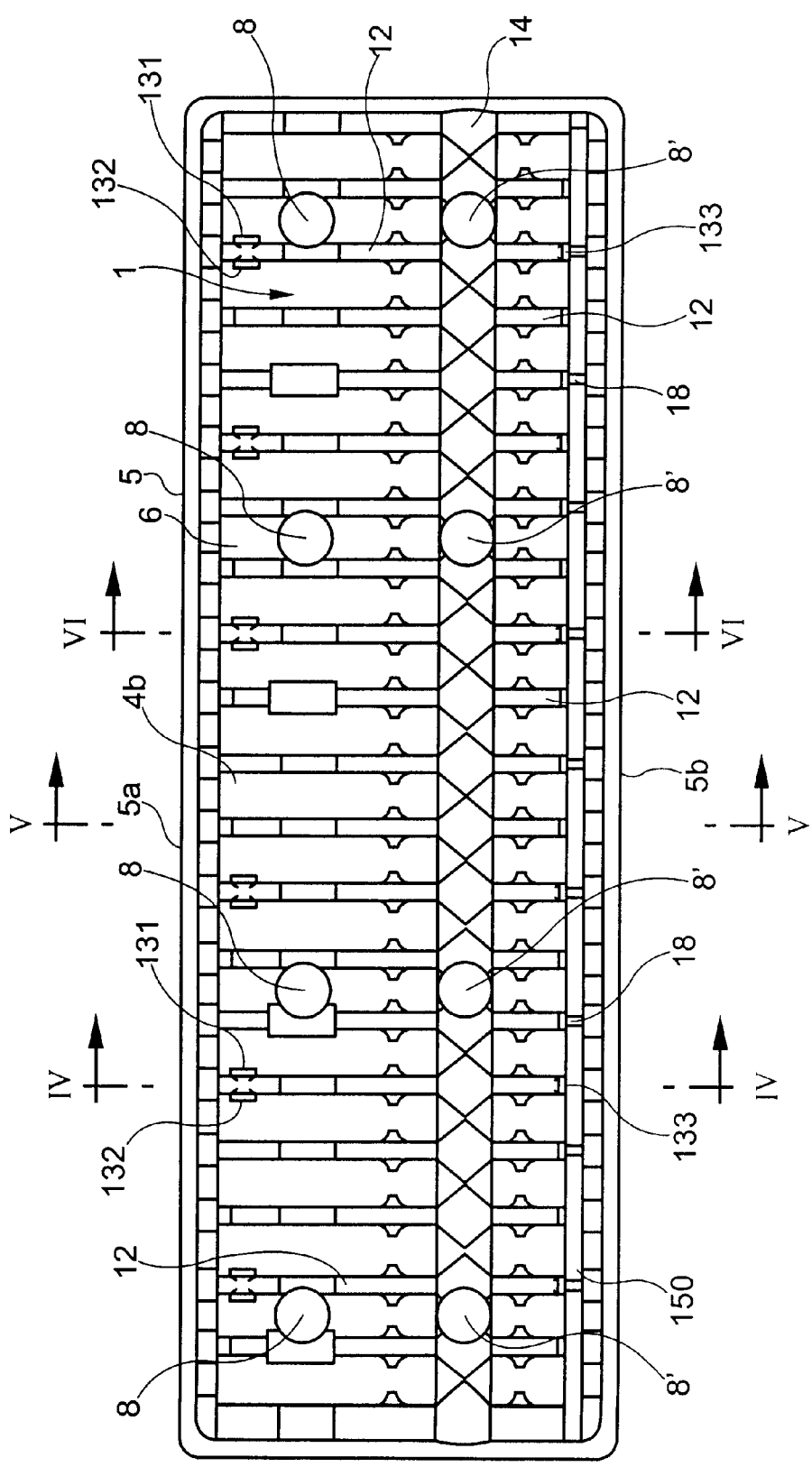
FIG. 2 is a bottom view of the tray of the present invention showing the second face of the tray as shown in FIG. 1.
Figure 3:
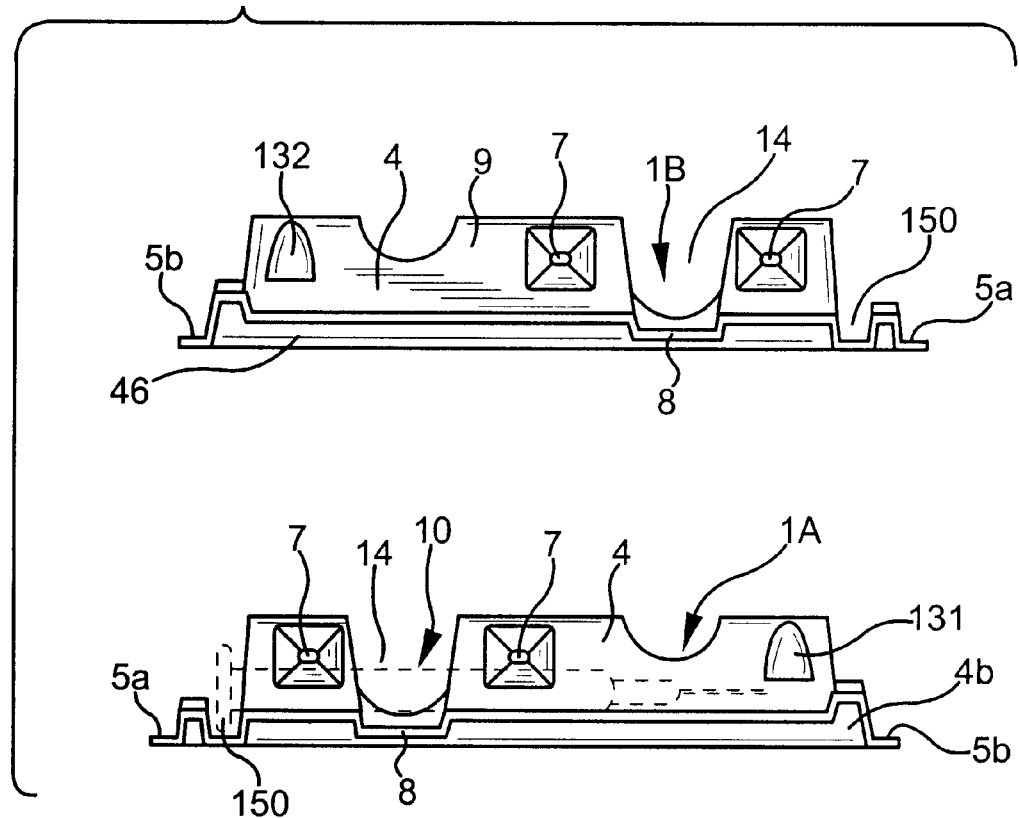
FIG. 3 is a side sectional view of the pair of trays illustrated in FIG. 1 taken along the line III—III as the trays are being stacked.

In the preferred embodiment, the tray is produced from a sheet of thermo-formed plastic material and as illustrated in FIGS. 1, 2 and 3 includes an elongated body 4 which has a generally rectangular shape and consequently extends in a first direction, or length, and in a second, transverse direction, or width. This tray also includes a first or upper face 4a visible in the lower part of FIG. 1, and a second, opposite or lower face 4b visible in the upper part of FIG. 1. A plurality of housings 6, which are open on the first face 4a, are intended to receive the syringes 10, respectively, for example syringes which are to be filled. These housings are each arranged in the second, transverse direction, or width, and are distributed in the first direction, or length. The intervals between successive housings 6 determine on the first face 4a, or upper face, transverse ribs 9, and on the second face, or lower face, transverse cavities 12 whose shape in terms of volume is adapted to that of the transverse ribs to allow stacking with nesting, particularly in alternate positions, of at least two trays, one being an upper tray 1B and the other being a lower tray 1A, for example. Each housing 6 includes opposite protuberances 7 which move back or elastically deflect in one direction for the insertion of the corresponding syringe 10, or syringe which is to be filled, and which, in the other direction hold it against gravity, what makes it possible to manipulate each tray upside down, even when it is loaded with the above mentioned syringes.

In accordance with the present invention, the elongated body 4 includes a plurality of studs 8, 8', for gripping, designed to come into contact with respectively, gripping vacuum pads of handling equipment (not shown), arranged and distributed over the second face 4b, or lower face, of body 4. As shown more clearly in the upper part of FIG. 1, each stud 8, 8' includes a flat area 8a, 8'a whose level is located in between lower and upper faces of the elongated body 4, that is to say above the support plane determined by the peripheral edges 5a and 5b of the body 4, in the position shown in FIG. 3. All the flat areas 8a, 8'a together determine two reference planes which are each set back with respect to the support plane defined previously. These two reference planes are consequently located inside the elongated body 4.

In particular, the studs 8, 8' are arranged, for example at an equal distance, on either side of the median longitudinal axis of the elongated body 4. For example, the studs 8, 8' are distributed in two gripping lines, each arranged between a longitudinal edge 5a and 5b and the median axis of the elongated body 4. According to this latter arrangement, the flat areas 8a of the studs 8 aligned in a first gripping line determine a reference plane at a different level, for example below or above the reference plane determined by the flat areas 8'a of the contact studs 8' aligned in the second gripping line. As stated above, the two reference planes are set back from the support plane of the elongated body 4, that is to say above the latter in the position of the trays 1A and 1B shown in FIGS. 4 and 5 for example.

As shown in FIGS. 1 and 3, the elongated body 4 includes an elongate trough 14 in the first direction, or length, which crosses the transverse housings 6 and transverse ribs 9, determining recesses 15 in the ribs 9.

As shown in FIG. 2, one of the gripping lines is aligned with the trough 14.

The reference plane determined by the flats 8'a of the studs 8' is slightly below the convex surface of the trough 14 along its summit line on the second-face 4b side. The reference plane determined by the flat areas 8a of the studs 8 is tangential to the convex surface of the housings 6 along their respective summit lines on the second-face 4b side.

By virtue of the arrangement of the studs 8, 8' described previously, the grouping trays according to the invention are compatible with handling equipment for gripping and manipulating conventional trays which predate the present invention.

Figure 6:
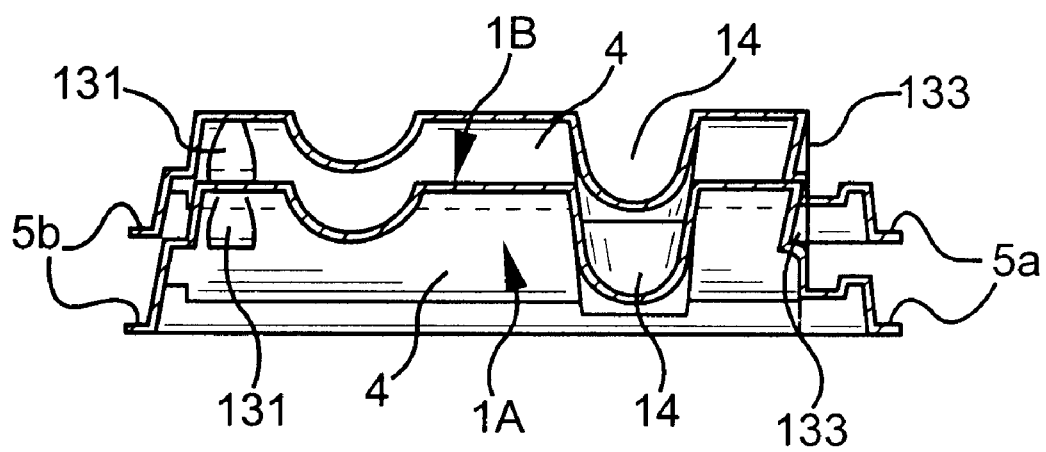
FIG. 6 is a side view of a pair of trays according to the present invention, which are not loaded, i.e., empty, stacked one on top of the other in normal positions, i.e., not alternating positions, as seen in section along the line VI—VI taken in FIG. 2.

As shown in greater detail in FIGS. 2 and 6, three stops 131, 132 and 133 are arranged inside one or more transverse ribs 9 of the trays for stacking them in a normal position (that is to say not an alternate position) without nesting.

More particularly, considering FIGS. 2 and 6, two transverse stops 131 and 132 are arranged in an opposing manner, on either side of one or more cavities 12, in order to come into contact with and to abut against the flattened summit 9a of one and the same rib 9 shown in FIG. 6.

Considering FIGS. 1 and 3 more particularly, the elongated body 4 includes an indent 150 arranged in the first direction, or length, on the same side as a longitudinal edge 5a of the elongated body 4, for receiving a portion of the collars 10b of the articles, or syringes 10, to be grouped together, respectively. In addition, a further longitudinal stop 133 shown in FIGS. 2, 4 and 6 is arranged on the same side as the indent 150 inside one or more transverse ribs 9 in order, also, to come into contact with the flattened summit 9a of a rib 9, on the side opposite the contact established with the same rib by the two stops 131 and 132.

The stops 131 to 133 allow stable stacking but prevents full nesting of the trays 1, in the empty state, that is to say before they are loaded with articles, for example syringes.

Figure 4:
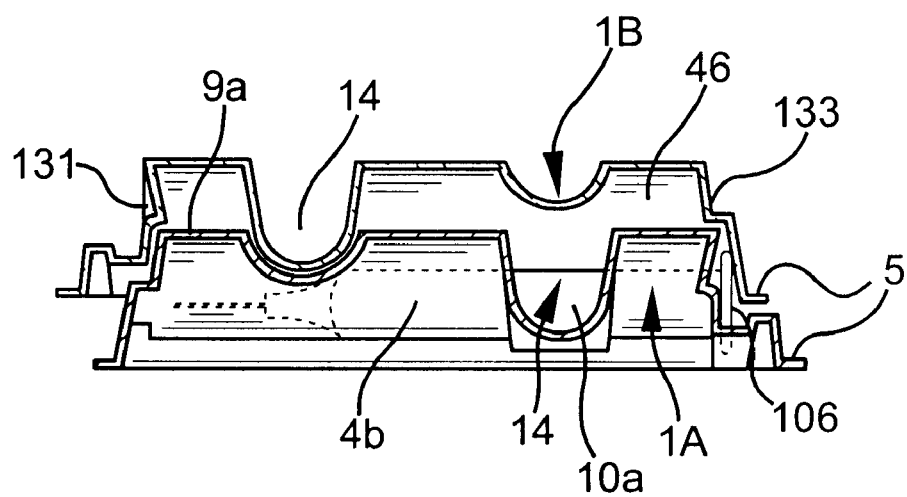
FIGS. 4 and 5 are side views of the pair of trays according to the present invention, loaded with syringes, stacked one on top of the other in alternating positions as seen in section, respectively, along the lines IV—IV and V—V taken in FIG. 2.
Figure 5:
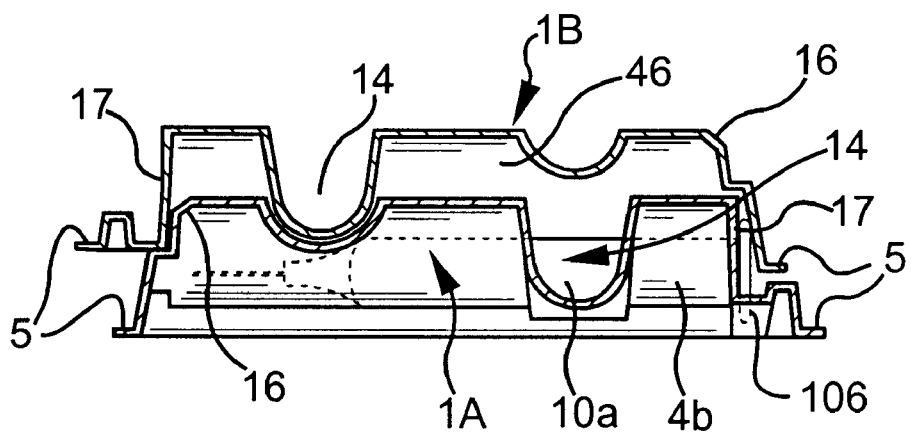

As shown more particularly in FIGS. 2, 4 and 5, the transverse ribs 9 have, for example in an alternate manner, positioning chamfers 16 and portions 17 which are not chamfered, but which are all located on the same side of the flattened body 4, for example on the same side as its longitudinal edge 5a. The indent 150 includes, on the first face 4a, solid portions 18 which interrupt it and serve to stiffen the longitudinal edge 5a of the elongated body 4. These portions or indents 18 also determine, on the second face 4b, hollowed-out portions for housing the non-chamfered portions 17, permitting self-positioning stacking of two successive trays 1A and 1B in alternate positions with respect to each other.

All the structural arrangements described and defined previously together give the tray significant dimensional tolerances for example of several millimeters, which makes it possible to automate handling and manipulation of the trays, including loaded trays, and makes it possible to use a thermo-forming process for producing them from a plastic material instead of the more accurate but expensive injection molding process.

By virtue of the chamfers 16, in particular alternate stacking of the loaded trays, 1A and 1B for example, takes place in a particularly simple manner, the trays being presented so that they are centered along the longitudinal median axis of the first tray 1A deposited on a stacking table. The offset of the tray 1B is achieved automatically, when said tray is released, through the action of the chamfers 16. In this way, the positioning of the trays 1A and 1B is obtained definitively, without having to offset said trays when they are presented for stacking, which simplifies the manipulation materials and machines.

While the present invention has been described in connection with syringes, it should be appreciated that it may be used in connection with other items or articles. Also, while the preferred embodiment of the present invention has been described so as to enable one skilled in the art to practice the tray of the present invention, it is to be understood that variations and modifications may be employed without departing from the concept and intent of the present invention as defined in the following claims. The preceding description is intended to be exemplary and should not be used to limit the scope of the invention. The scope of the invention should be determined only by reference to the following claims.

What is claimed is:

1. A tray for grouping together syringes each having a collar wherein the syringes are to be filled with medicinal products, said tray comprising:

a body portion which includes a first face and a second face which are opposite each other, said body portion being elongate in a first direction;

said body portion including a plurality of housings which are open on the first face for said syringes, respectively each arranged in a second, transverse direction and at least one stop, said housings being separated by transverse ribs distributed in the first direction on the first face and transverse cavities on the second face, the shape of the transverse cavities corresponding in terms of volume to the transverse ribs being adapted to that of the transverse cavities to allow stable stacking of the tray with another tray so that the at least one stop with respect to another tray is arranged inside a transverse rib;

said body portion also including an indent arranged in the first direction, on the same side as a longitudinal edge of said body portion, for receiving a portion of a collar of each syringe, respectively, wherein another stop is arranged on the same side as the indent;

at least one of said transverse ribs having a positioning chamfer and a portion which is not chamfered and, in a corresponding manner, the indent includes, on the first face, at least one solid portion which interrupts it, determining, on the second face, at least one hollowed-out portion for housing the non-chamfered portion so that said tray may be stacked with another tray in alternate positions relative to a vertical axis of each tray with respect to each other; and each housing including opposite protuberances which deflect in one direction for the insertion of the corresponding syringe and which, in the other direction, hold the same syringe, wherein the second face of said body portion includes a plurality of gripping studs each including a flat area whose level is located inside the body portion above a support plane of the tray so that a suction force may be applied to the flat area of said gripping studs for handling the tray, with the gripping studs being arranged and distributed over the second face.

2. The tray as claimed in claim 1, wherein the gripping studs are arranged on the second side of a longitudinal median axis of the body portion.

3. The tray as claimed in claim 2, wherein the gripping studs are distributed in two gripping lines, with each stud arranged between a longitudinal edge and the longitudinal median axis of the body portion.

4. The tray as claimed in claim 3, wherein the flat areas of the gripping studs aligned in a first gripping line determine a reference plane at a level which is different from that of the reference plane determined by the flat areas of the contact studs aligned in the second gripping line.

5. The tray as claimed in claim 2, according to which said body portion includes an elongate trough in the first direction which crosses said housings, wherein a gripping line is aligned with the trough.

6. The tray as claimed in claim 2, wherein the gripping studs are aligned in pairs with the housing.

7. The tray as claimed in claim 1, wherein two transverse stops are arranged in an opposing manner, on either side of the traverse ribs for coming into contact with the flattened summit of the traverse rib and a traverse rib of another tray when two or more trays are stacked.

* * * * *